(12) United States Patent
Shiga et al.

(10) Patent No.: US 7,407,917 B2
(45) Date of Patent: Aug. 5, 2008

(54) LUBRICATING OIL COMPOSITION FOR AUTOMATIC TRANSMISSIONS

(75) Inventors: Michio Shiga, Hiratsuka (JP); Tomotusgu Shiroi, Shizuoka Prefecture (JP)

(73) Assignee: Chevron Oronite Company LLC, San Ramon, CA (US)

( * ) Notice: Subject to any disclaimer, the term of this patent is extended or adjusted under 35 U.S.C. 154(b) by 554 days.

(21) Appl. No.: 10/989,451

(22) Filed: Nov. 16, 2004

(65) Prior Publication Data

US 2005/0124506 A1 Jun. 9, 2005

(30) Foreign Application Priority Data

Nov. 17, 2003 (JP) ............................. 2003-387033

(51) Int. Cl.
- *C10M 139/00* (2006.01)
- *C10M 137/00* (2006.01)
- *C10L 1/22* (2006.01)
- *C10G 71/00* (2006.01)
- *C09K 5/00* (2006.01)

(52) U.S. Cl. .................. 508/194; 508/189; 508/441; 508/442; 508/454; 208/18; 208/19; 252/77

(58) Field of Classification Search ............... 508/194, 508/189, 454, 441, 442; 208/18, 19; 252/77, 252/47, 47.5, 33, 56 R
See application file for complete search history.

(56) References Cited

U.S. PATENT DOCUMENTS

| | | | | |
|---|---|---|---|---|
| 4,136,043 A | * | 1/1979 | Davis | 508/231 |
| 4,326,972 A | * | 4/1982 | Chamberlin, III | 508/331 |
| 4,426,305 A | * | 1/1984 | Malec | 508/192 |
| 4,471,091 A | * | 9/1984 | Hayashi | 525/71 |
| 4,948,523 A | * | 8/1990 | Hutchison et al. | 508/273 |
| 4,952,328 A | * | 8/1990 | Davis et al. | 508/237 |
| 5,137,980 A | * | 8/1992 | DeGonia et al. | 525/327.6 |
| 5,346,637 A | * | 9/1994 | Horodysky et al. | 508/508 |
| 5,395,539 A | | 3/1995 | Chandler et al. | |
| 5,712,230 A | * | 1/1998 | Abraham et al. | 508/232 |
| 5,916,852 A | | 6/1999 | Nibert et al. | |
| 6,303,547 B1 | * | 10/2001 | Balasubramaniam | 508/454 |
| 6,451,745 B1 | * | 9/2002 | Ward | 508/192 |
| 6,482,779 B2 | * | 11/2002 | Naka et al. | 508/379 |
| 2001/0044388 A1 | * | 11/2001 | Sivik et al. | 508/232 |
| 2002/0072478 A1 | | 6/2002 | Ishida et al. | |
| 2004/0192564 A1 | * | 9/2004 | Balasubramaniam et al. | 508/436 |

FOREIGN PATENT DOCUMENTS

| | | |
|---|---|---|
| GB | 878519 | 10/1961 |
| JP | 2001-247532 | 9/2001 |
| JP | 3330245 B2 | 9/2002 |
| JP | 2004175818 A * | 6/2004 |

* cited by examiner

*Primary Examiner*—Glenn Caldarola
*Assistant Examiner*—Huy-Tram Nguyen
(74) *Attorney, Agent, or Firm*—Jones Day; Steven G.K. Lee

(57) ABSTRACT

An additive compound comprising a non-borated and/or borated reaction product, in which the reaction product is obtained by reacting a linear or branched, saturated or unsaturated monovalent aliphatic acid having 8 to 22 carbon atoms, urea, and polyalkylenepolyamine, when employed in a lubricating oil composition is favorably employable as an automatic transmission fluid of internal combustion engines.

16 Claims, No Drawings

LUBRICATING OIL COMPOSITION FOR AUTOMATIC TRANSMISSIONS

The present invention relates to an additive compound and a lubricating oil composition. In particular, the invention relates to an additive compound favorably employable in a lubricating oil composition for automatic transmissions of internal combustion engines, in which the lubricating oil composition shows a high torque transmissive capacity and a prolonged shudder inhibition.

BACKGROUND OF THE INVENTION

Automatic transmissions in automobiles comprise a torque converter, a wet multi-plate clutch, a gear mechanism, and a mechanism controlling these elements. The torque transmission capacity is automatically set according to the speed of automobile and the degree of load. Modern automatic transmissions further comprise a lockup clutch mounted to the torque converter, so as to improve fuel economy. The use of the lockup clutch enables engine torque to be transmitted to the automatic transmission according to driving conditions in addition to the driving force transmitted through a lubricating oil. However, since the torque variation produced by the operation of the lockup clutch sometimes disturbs passengers due to shudder, the lockup clutch is generally set to operate only under high speed driving conditions giving less torque variation.

Under low speed driving conditions as when an automobile starts, loss of driving force transmission is caused between the engine output revolution and the transmission input revolution. Therefore, enough improvement of fuel economy is not attained. Accordingly, automatic transmissions adopt a slip control system by which the lockup mechanism can operate under the low speed driving conditions and the transmission loss can be reduced. However, when the clutch is subjected to control by the slip control system, abnormal vibration of the body of automobile (i.e., shudder) takes place on the friction surface of the lockup clutch. At low road speeds vehicle operation is rough and engine vibration is transmitted through the drive train. Rough operation and engine vibration are not acceptable to drivers.

Shudder occurs when the sliding rate (V) in the lockup clutch increases and the coefficient of friction ($\mu$) decreases. Thus, it is desirable to employ a lubricating oil (automatic transmission fluid) which shows a favorable $\mu$-V character, i.e., the friction coefficient increases when the sliding rate increases, and keeps the favorable $\mu$-V character for a prolonged period of time, i.e., prolonged shudder inhibition performance.

JASO (Japanese Automobile Standard Organization) M349:2001 describes a standard oil T-III which shows standard shudder inhibition performance and transmissive torque capacity. However, there is given no information with respect to formulation of the T-III standard oil.

Prolonged shudder inhibition can be attained by incorporating a friction modifier (generally, friction decreasing agent). However, if too much friction modifier is incorporated into a lubricating oil, the friction coefficient of the wet clutch extremely decreases and hence enough transmissive torque capacity cannot be obtained.

U.S. Pat. No. 4,948,523 discloses a lubricating composition, preferably essentially free of zinc dihydrocarbyldithiophosphate compounds, and optionally free of chlorine containing silver lubricity agents, comprising a major proportion of an oil of lubricating viscosity and a minor amount of a silver protective agent comprising the reaction product of a $C_5$ to $C_{60}$ carboxylic acid and at least one amine selected from the group consisting of (1) guanidine, urea, and thiourea compounds; (2) $C_1$ to $C_{20}$ hydrocarbyl or hydroxy-substituted hydrocarbyl mono-amines, alkylene diamines, and (3) polyalkylene polyamines; and N-alkyl glycine.

U.S. Pat. No. 5,395,539 discloses certain hydrocarbon soluble or dispersible amide reaction products (Component-1), and mixtures, and/or acid amine salts of Component-1 and certain acid/esters (Component-2), which are useful as friction modifying additives for oleaginous compositions such as lubricating oils, including power transmitting fluids, particularly automatic transmission fluids (ATF), and to the oleaginous compositions in which they are contained.

U.S. Pat. No. 5,916,852 discloses lubricating fluids which include an additive combination comprising a compound having the general formula R—$NH_2$ with oil-soluble phosphorus compounds, an ashless dispersant, and, optionally, other amine containing friction modifiers provide lubricating fluids which exhibit excellent break-in characteristics that are capable of preventing green shudder in automatic transmissions.

U.S. Pat. No. 6,303,547 discloses lubricant formulations containing the reaction product of at least one $C_5$ to $C_{60}$ carboxylic acid and at least one amine selected from the group consisting of guanidine, aminoguanidine, urea, thiourea and salts thereof is useful as a gear oil additive. The lubricant formulations exhibit excellent low and high temperature rheology and are particularly suited for use in automotive and industrial gear applications. Lubricants of the present invention exhibit improved performance properties, such as increased axle efficiencies and lower axle temperatures, improved limited slip performance, reduced chatter, improved frictional durability and/or improved power divider performance compared to lubricant formulations that do not contain said reaction products.

Japanese Patent Publication No. 2001-247532 discloses fatty acid amide compounds used for surface lubricant, vehicle component and thermal recording materials, has three or more amide groups in a molecule having the formula $R_1CONH(CH_2)_m((NCOR_2)(CH_2)_n)_lNHCOR_3$, where $R_1$-$R_3$ is a $C_{12}$ to $C_{50}$ alkyl or alkenyl group, m and n=1-3, and l=1-4.

U.S. Patent Application Publication No. 2002/0072478A1 discloses a lubricating oil and one or more succinimide-modified compounds having long-lasting anti-shudder property, enhanced transmission torque capacity for a wet clutches and/or wet brakes, and an excellent shifting property for automatic transmissions and continuously variable transmissions.

Japanese Patent No. 3330245 discloses lubricating oil compositions for slide guide surfaces containing nitrogen-containing compounds of polyamines and amides in mineral and/or synthetic oil.

SUMMARY OF THE INVENTION

The present invention provides an additive compound employable in a lubricating oil composition for automatic transmissions in internal combustion engines. The lubricating oil composition employing the additive compound of the present invention has a high transmissive torque capacity and prolonged shudder inhibition when used as an automatic transmission fluid (ATF) in automatic transmissions of internal combustion engines.

It is desirable that an automatic transmission fluid not only should show a high shudder inhibiting ability when the transmission fluid is first used, but also should keep the high shudder inhibiting ability for a prolonged period of time without substantial decrease of the inhibiting ability and further should show a high transmissive torque capacity.

Accordingly, the present invention relates to an additive compound employable in a lubricating oil composition having the beneficial performances mentioned above.

The additive compound of the present invention employable in the lubricating oil composition comprises the reaction product of a linear or branched, saturated or unsaturated monovalent aliphatic acid having 8 to 22 carbon atoms, urea, and polyalkylenepolyamine, wherein the reaction product is non-borated, borated or a mixture thereof.

The present invention furthermore relates to a lubricating oil composition comprising a major amount of base oil of lubricating viscosity and a minor amount of the reaction product of a linear or branched, saturated or unsaturated monovalent aliphatic acid having 8 to 22 carbon atoms, urea, and polyalkylenepolyamine, wherein the reaction product is non-borated, borated or a mixture thereof.

The present invention further relates to a method of reducing shudder in an automatic transmission of an internal combustion engine by adding the lubricating oil composition of the present invention to an automatic transmission and operating the engine.

Among other factors, the present invention is based on the surprising discovery that an additive compound comprising a non-borated and/or borated reaction product, in which the reaction product is obtained by reacting a linear or branched, saturated or unsaturated monovalent aliphatic acid having 8 to 22 carbon atoms, urea, and polyalkylenepolyamine, provides high transmissive torque capacity and prolonged shudder inhibition when employed as a lubricating oil in an automatic transmission of an internal combustion engine. The lubricating oil composition employing the additive compound is useful as a method for reducing shudder when used as an automatic transmission fluid. Accordingly the present invention is also directed to the use of the present additive compound in an automatic transmission fluid to reduce shudder in an automatic transmission of an internal combustion engine.

DETAILED DESCRIPTION OF THE INVENTION

The preferred embodiments of the additive compound and lubricating oil composition according to the present invention will be described in further detail below.

The Additive Compound

The additive compound of the present invention employable in the lubricating oil composition of the present invention may be a non-borated (A) and/or borated (B) reaction product in which the reaction product is obtained by reacting a linear or branched, saturated or unsaturated monovalent aliphatic acid having 8 to 22 carbon atoms, urea, and polyalkylenepolyamine. The additive compounds A and B can be employed singly or in combination.

Additive compound A comprises the reaction product of a linear or branched, saturated or unsaturated monovalent aliphatic acid having 8 to 22 carbon atoms, urea, and polyalkylenepolyamine.

Additive compound B comprises the borated reaction product in which the reaction product is obtained by reacting a linear or branched, saturated or unsaturated monovalent aliphatic acid having 8 to 22 carbon atoms, urea, and polyalkylenepolyamine.

Monovalent Aliphatic Acid

The monovalent aliphatic acid is a compound which is represented by the formula:

$$R_4(COOH)_y$$

or anhydride thereof, wherein R4 represents a hydrocarbyl group having about 2 to 50 carbon atoms, and y represents an integer of 1-4.

The monovalent aliphatic acid employed for the preparation of the additive compound of the present invention is a linear or branched, saturated or unsaturated monovalent aliphatic acid containing 8 to 22 carbon atoms. Examples of the aliphatic acids include octanoic acid, lauric acid, myristic acid, palmitic acid, stearic acid, isostearic acid, oleic acid, and behenic acid. Particularly preferred is isostearic acid.

Urea

Any ordinarily employable urea such as urea of industrial purity grade can be employed.

Polyalkylenepolyamine

Preferred is a polyalkylenepolyamine containing 2 to 30 carbon atoms and 2 to 15 nitrogen atoms, each of at least two nitrogen atoms constituting primary amine. Preferably, the alkylene groups of such polyalkylenepolyamines will contain form 2 to 6 carbon atoms, more preferably form 2 to 4 carbon atoms. The nitrogen atom other than the nitrogen atoms constituting primary amine generally constitutes secondary amine.

Examples of suitable polyalkylene polyamines include ethylenediamine, propylenediamine, isopropylenediamine, butylenediamine, pentylenediamine, hexylenediamine, diethylenetriamine, dipropylenetriamine, dimethylaminopropylamine, diisopropylenetriamine, dibutylenetriamine, di-sec-butylenetriamine, triethylenetetraamine, tripropylenetetraamine, triisobutylenetetraamine, tetraethylenepentamine, pentaethylenehexamine, hexaethyleneheptamine, dimethylaminopropylamine, and mixtures thereof.

Particularly suitable polyalkylene polyamines are those having the formula:

$$H_2N-(R_5NH)_z-H$$

wherein $R_5$ is a straight- or branched-chain alkylene group having 2 to 6 carbon atoms, preferably 2 to 4 carbon atoms, most preferably about 2 carbon atoms, i.e., ethylene ($-CH_2CH_2-$); and z is an integer from 1-4, preferably 1-2.

Particularly preferred polyalkylene polyamines are ethylenediamine, diethylenetriamine, triethylenetetraamine, tetraethylenepentamine, pentaethylenehexamine, and hexaethyleneheptamine. Particularly preferred is hexaethyleneheptamine.

Many of the polyamines suitable for use in the present invention are commercially available and others may be prepared by methods that are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99-116.

The additive compound of the present invention can be obtained by reacting the acid compound (i.e., monovalent aliphatic acid), urea, the amine compound (i.e., polyalkylenepolyamine) in such conditions (i.e., ratio and nature) that the resulting reaction compound shows an oil-soluble property. The additive compound of the present invention is preferably obtained by reacting one mole of the monovalent aliphatic acid, 0.01 to 2 moles (preferably 0.03 to 0.5 moles) of urea, and 0.1 to 1 mole (preferably 0.125 to 0.5 moles) of polyalkylenepolyamine. The reaction can be performed generally at 100-250° C., preferably at 150-200° C., generally for 1-30 hours, preferably for 2-6 hours. Since the reaction is a condensation reaction, it is preferred that the produced water is removed continuously. The progress of the reaction can be checked by measuring the production of water.

The above-mentioned reaction product can be preferably borated by the reaction using a boric acid compound to yield the borated additive compound (B). The reaction can be carried out by adding to the above-mentioned reaction product a solid boric acid compound in such amount that the amount of boron in the boric acid compound is 0.001 to 0.25 weight part based one weight part of nitrogen in the above-mentioned reaction product, and heating the mixture to 100-160° C. at an atmospheric pressure or a reduced pressure (reduced to 6.7 kPa) for 5-12 hours. The reaction is preferably continued until the solid boric acid compound diminishes in the reaction mixture.

Lubricating Oil Composition

The present invention also relates to a lubricating oil composition containing the additive compound of the present invention. Such a lubricating oil composition will comprise a major amount of base oil of lubricating viscosity and a minor amount of the additive compound of the present invention (A and/or B) as described above.

Base oil as used herein is defined as a base stock or blend of base stocks which is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100° Centigrade (C) and about 4 centistokes (cSt) to about 20 cSt. Hydrocarbon synthetic oils may include, for example, oils prepared from the polymerization of ethylene, polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity about 20 cSt or higher at about 100 C. Oils used as the base oil will be selected or blended depending on the desired end use and the additives in the finished oil to give the desired grade of engine oil, e.g. a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, or 15W-40.

There are no specific conditions with respect to the base oil, provided that the base oil is selected from the base stocks generally employed for preparing lubricating oil compositions. The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in Table 1. Group IV base oils are polyalphaolefins (PAO). Group V base oils include all other base oils not included in Group I, II, III, or IV. Group III base oils are preferred.

TABLE 1

Saturates, Sulfur and Viscosity Index of Group I, II, III, IV and V Base Stocks

| Group | Saturates (As determined by ASTM D2007) Sulfur (As determined by ASTM D2270) | Viscosity Index (As determined by ASTM D4294, ASTM D4297 or ASTM D3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |
| IV | All Polyalphaolefins (PAOs) | |
| V | All others not included in Groups I, II, III, or IV | |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil.

Such wax isomerate oil is produced by the hydroisomerization of natural or synthetic waxes or mixtures thereof over a hydroisomerization catalyst.

It is preferred to use a major amount of base oil in the lubricating oil of the present invention. A major amount of base oil as defined herein comprises 40 wt % or more. Preferred amounts of base oil comprise 40 to 99.9 wt %, preferably greater than 50 to 97 wt %, more preferably 60 to 97 wt % of the lubricating oil composition. (When weight percent is used herein, it is based on the total weight percent of the lubricating oil composition unless otherwise specified.)

The additive composition of the present invention in the lubricating oil composition will be in a minor amount compared to the base oil of lubricating viscosity. Generally, it will be in an amount from 0.1 to 10 wt %, preferably from 0.3 to 5 wt % and more preferably from 0.3 to 2.0 wt % based on the total weight of the lubricating oil composition.

The lubricating oil composition of the present invention can further contain various lubricating oil additives available in the art. Examples of the optionally incorporable additives include viscosity index improvers, ashless dispersants, metal-containing detergents, anti-wear agents, friction modifiers, oxidation inhibitors, corrosion inhibitors, seal swelling agents, dyes, and pour point depressants. Particularly preferred additive is diphenyl hydrogen phosphite which is known as an anti-wear agent.

A number of the above-mentioned optionally incorporable additives are well known. Details of such additives are described below.

Viscosity Index Improver

Examples of the viscosity index improvers include non-dispersant type viscosity index improvers such as copolymers of various methacrylic acid esters and one or more other monomers and their hydrogenated products and dispersant type viscosity index improvers such as copolymers of various methacrylic acid esters and nitrogen-containing monomers. Other non-dispersant type or dispersant type viscosity index improvers such as copolymers of ethylene and α-olefins (e.g., propylene, 1-butene, and 1-pentene) and their hydrogenated products, and polyacrylic acid esters are also useful in the present invention.

The lubricating oil composition of the present invention generally contains a viscosity index improver in an amount of 1 to 20 wt. %, preferably 1 to 8 wt. %.

Ashless Dispersant

Alkenyl- or alkyl-succinimide or its derivative is the preferred ashless dispersant. The alkenyl- or alkyl-group can be derived from polyolefin. The nitrogen-atom containing compound is preferably contained in the lubricating oil composition in an amount of 0.01 to 0.3 wt. % in terms of the nitrogen content. A representative succinimide can be prepared by the reaction between succinic anhydride having a high molecular weight alkenyl or alkyl substituent group with polyalkylenepolyamine containing 4 to 10 nitrogen atoms (average, preferably 5 to 7 nitrogen atoms) in one molecule. The high molecular weight alkenyl or alkyl substituent group is preferably derived from polyolefin having a number average molecular weight of approx. 900 to 5,000. A particularly preferred polyolefin is polybutene.

The process for preparing the polybutenylsuccinic anhydride by the reaction between polybutene and maleic anhydride is generally performed by a chlorination method utilizing chlorine. While this reaction is advantageous in giving a high reaction yield, it has disadvantageous feature in that a large amount (for instance, approx. 2,000 ppm) of chlorine remains in the finally obtained succinimide product. In contrast, a thermal reaction process utilizing no chlorine gives a final reaction product having extremely low chlorine content (such as 40 ppm or less). It is known that an improved thermal reaction process employing a highly reactive polybutene (containing at least approx. 50% of methylvinylidene structure) in place of the conventional polybutene (containing mainly β-olefin structure) gives a high reaction yield. The improved thermal reaction process is further advantageous because a reaction ratio of the polybutene increases and the resulting dispersant contains the effective product (succinimide) in a high concentration. Accordingly, it is preferred that the polybutenylsuccinic anhydride is produced from the highly reactive polybutene converted by a thermal process and the resulting polybutenylsuccinic anhydride is converted into succinimide by the reaction with polyalkylenepolyamine containing 4 to 10 nitrogen atoms (average per one molecule). The resulting succinimide can be further converted to a modified succinimide by a further reaction with boric acid, alcohol, aldehyde, ketone, alkylphenol, cyclic carbonate, organic acids, or inorganic acids such as phosphoric acid. From the thermal stability and oxidation stability, particularly preferred is a boron-containing alkenyl- or alkyl-succinimide which is produced by the reaction with boric acid or a boron-containing compound.

Other ashless additives such as alkenylbenzylamine compounds and alkenylsuccinic acid esters can be employed independently or in combination with the above-mentioned alkenyl- or alkyl-succinimide or its derivative.

Metal-Containing Detergent

Generally, a metal-containing detergent, i.e., metal atom-containing detergent, having a total base number of 10 to 500 mg·KOH/g is employed in an amount of 0.01 to 2.0 wt. %. Examples of the metal-containing detergents include alkaline earth metal salts of petroleum sulfonic acids, alkylbenzenesulfonic acids, and alkyloxybenzenesulfonic acids or their over-based products. The alkaline earth metal salts preferably are Mg salts or Ca salts. The metal-containing detergents can be employed singly or in combination. Otherwise, phenate sulfide or salicylate can be employed singly or in combination.

Anti-Wear Agent and Friction Modifier

It is preferred that the lubricating oil composition of the present invention further contains diphenyl hydrogen phosphite which serves as an anti-wear agent and a friction modifier. The static friction coefficient retention of the lubricating oil composition of the present invention is further improved by the incorporation of diphenyl hydrogen phosphite. The diphenyl hydrogen phosphite is generally contained in the lubricating oil composition of the present invention in an amount of 0.01 to 2 wt. %, preferably 0.05 to 0.5 wt. %.

Other phosphoric acid esters, phosphoric acid amine salts, phosphorous acid esters, and phosphorous acid amine salts can be incorporated into the lubricating oil composition of the present invention independently or in addition to diphenyl hydrogen phosphite. Examples of these compounds include aromatic tertiary phosphites such as triphenyl phosphite and tris(nonylphenyl) phosphite; aliphatic tertiary phosphites such as triethyl phosphite, trioctyl phosphite, tridecyl phosphite, trilauryl phosphite, tris(tridecyl) phosphite, tristearyl phosphite, and trioleyl phosphite; aliphatic secondary phosphites such as dibutyl hydrogen phosphite, dioctyl hydrogen phosphite, didecyl hydrogen phosphite, dilauryl hydrogen phosphite, and dioleyl hydrogen phosphite; aromatic or aliphatic phosphoric triesters such as triphenyl phosphate, tricresyl phosphate, tributyl phosphate, trioctyl phosphate, trilauryl phosphate, tristearyl phosphate, and trioleyl phosphate; and aliphatic acidic phosphoric acid esters such as methyl acid phosphate, ethyl acid phosphate, butyl acid phosphate, octyl acid phosphate, decyl acid phosphate, dodecyl acid phosphate, tridecyl acid phosphate, stearyl acid phosphate, and oleyl acid phosphate. Examples of the amine salts include linear or branched aliphatic amine compounds having 8 to 18 carbon atoms such as octylamine, decylamine, laurylamine, caprylamine, coconut amine, tallow oil amine, and oleylamine.

If desired, zinc dialkyldithiophosphate, which is a known additive serving as an anti-wear agent, an oxidation inhibitor, and an extreme-pressure agent, can be incorporated into the lubricating oil composition of the present invention.

Oxidation Inhibitor

It is preferred that the lubricating oil composition of the present invention further contains an oxidation inhibitor such as a hindered phenol compound, a diarylamine compound, or a molybdenum compound in an amount of 0.01 to 5 wt. % based on the amount of the lubricating oil composition.

Examples of the hindered phenol compounds include 2,6-di-t-butyl-p-cresol, 4,4'-methylenebis(2,6-di-t-butylphenol), 4,4'-methylenebis(6-t-butyl-o-cresol), 4,4'-isopropylidenebis(2,6-di-t-butylphenol), 4,4'-bis(2,6-di-t-butylphenol), 2,2'-methylenebis (4-methyl-6-t-butylphenol), 4,4'-thiobis(2-methyl-6-t-butylphenol), 2,2-thiodiethylenebis[3-(3,5-di-t-butyl-4-hydroxyphenyl)propionate], octyl 3-(3,5-di-t-butyl-4-hydroxypheny)propionate, octadecyl 3-(3,5-di-t-butyl-4-hydroxyphenyl)propionate and octyl 3-(5-t-butyl-4-hydroxy-3-methylphenyl)propionate.

Examples of the diarylamine compounds include an alkyldiphenylamine containing a mixture of alkyl groups having 4 to 9 carbon atoms, p,p'-dioctyldiphenylamine, phenyl-α-naphthylamine, phenyl-β-naphthylamine, alkylated α-naphthylamine, and alkylated phenyl-α-naphthylamine. Each of the hindered phenol compounds and diarylamine compounds can be used singly or in combination. Other oil soluble oxidation inhibitors can be employed in combination.

The oxidation inhibitor can be a molybdenum-containing compound which is a multi-functional additive. The molybdenum-containing compound is preferably contained in the lubricating oil composition in an amount of 30 to 1,000 ppm in terms of the molybdenum content.

Examples of the molybdenum-containing compounds are molybdenum-containing imide, amide or amine compounds. Sulfur-containing oxymolybdenum-succinimide complex compound can improve high temperature detergency and oxidation inhibition, and hence is favorably employed. Sulfated oxymolybdenum dithiocarbamate and sulfated oxymolybdenum dithiophosphate can improve oxidation inhibition, wear inhibition, and reduction of friction coefficient, and hence are favorably employed.

Dye

When the lubricating oil composition of the present invention is employed as an ATF, the oil composition is preferably colored by a dye such as red dye.

Corrosion Inhibitor

The corrosion inhibitor preferably is a copper corrosion inhibitor. The copper corrosion inhibitor can be a thiazole compound, a triazole compound or a thiadiazole compound. Examples of these compounds include benzotriazole, tolyltriazole, octyltriazole, decyltriazole, dodecyltriazole, 2-mercaptobenzothiazole, 2,5-dimercapto- 1,3,4-thiadiazole, 2-mercapto-4-hydrocarbyldithio-1,3,4-thiadiazole, and 2,5-bis(hydrocarbyldithio)-1,3,4-thiadiazole.

Other employable corrosion inhibitors include alkenylsuccinic acid and its anhydride. Examples of these compounds include tetrapropenylsuccinic acid, tetrapropenylsuccinic anhydride, tetradocenylsuccinic acid, tetradocenylsuccinic anhydride, octadecenylsuccinic acid, and octadecenylsuccinic anhydride. Otherwise, an alkenylsuccinic acid having an alkenyl group of 8 to 24 carbon atoms, and a half ester of this alkenylsuccinic acid and an alcohol such as polyglycol can be employed as corrosion inhibitor.

In addition, an amine compound, an acidic phosphoric acid ester, an ethoxylated amine compound, an imidazoline compound, an aminosuccinic acid, or their derivatives can be employed as corrosion inhibitor.

Pour Point Depressant

Examples of the pour point depressants include polymethacrylic acid esters, polyacrylic acid esters, polyacrylamides, condensation products of paraffin wax and aromatic compounds.

Seal Swelling Agent

When the lubricating oil composition of the present invention is used as an ATF, a seal swelling agent which swells elastomer sealing material placed in the automatic transmission system may be used. Examples of the seal swelling agents include oil-soluble dialkylesters of dibasic acids such as adipic acid, azelaic acid, sebacic acid, or phthalic acid. Examples of preferred seal swelling agents include an adipic acid ester, an azelaic acid ester or a sebacic acid ester of an alkanol having 8 to 13 carbon atoms, and a phthalic acid ester of an alkanol having 4 to 13 carbon atoms.

EXAMPLES

The invention will be further illustrated by the following examples, which set forth particularly advantageous method embodiments. While the Examples are provided to illustrate the present invention, they are not intended to limit it. This application is intended to cover those various changes and substitutions that may be made by those skilled in the art without departing from the spirit and scope of the appended claims.

Example 1

Preparation of Additive Compound A1
(Non-Borated)

In a four-necked flask equipped with a stirrer, a thermometer, and a dehydrating device were placed 1,034 g (3.5 moles) of isostearic acid and 15 g (0.25 moles) of urea. The resulting mixture was heated to 100° C., and 137.5 g (0.5 moles) of hexaethyleneheptamine was dropwise added to the heated mixture under replacement of the reaction atmosphere with nitrogen gas. After the addition was complete, the reaction mixture in the flask was gradually heated to reach 160° C. within 3 hours. Water produced by the reaction caused in the course of heating was removed from the flask. Finally, the pressure of inside of the flask was reduced to 6.7 kPa, so as to completely remove the produced water. Finally obtained reaction product (Additive Compound A1) was a brown liquid having 4.3 wt. % of nitrogen content.

Example 2

Preparation of Additive Compound A2
(Non-Borated)

In a four-necked flask equipped with a stirrer, a thermometer, and a dehydrating device were placed 738 g (2.5 moles) of isostearic acid and 15 g (0.25 moles) of urea. The resulting mixture was heated to 100° C., and 95 g (0.5 moles) of tetraethylenepentamine was dropwise added to the heated mixture under replacement of the reaction atmosphere with nitrogen gas. After the addition was complete, the reaction mixture in the flask was gradually heated to reach 160° C. within 3 hours. Water produced by the reaction caused in the course of heating was removed from the flask. Finally, the pressure of inside of the flask was reduced to 6.7 kPa, so as to completely remove the produced water. Finally obtained reaction product (Additive Compound A2) was a brown liquid having 4.2 wt. % of nitrogen content.

Example 3

Preparation of Additive Compound B (Borated)

In a four-necked flask equipped with a stirrer, a thermometer, and a dehydrating device were placed 1,034 g (3.5 moles) of isostearic acid and 15 g (0.25 moles) of urea. The resulting mixture was heated to 100° C., and 137.5 g (0.5 moles) of hexaethyleneheptamine was dropwise added to the heated mixture under replacement of the reaction atmosphere with nitrogen gas. After the addition was complete, the reaction mixture in the flask was gradually heated to reach 160° C. within 3 hours. Water produced by the reaction caused in the course of heating was removed from the flask. Finally, the pressure of inside of the flask was reduced to 6.7 kPa, so as to completely remove the produced water. Then, the pressure of inside of the flask was returned to atmospheric pressure. The reaction product was cooled to 100° C., and 9.3 g (0.15 moles) of boric acid was added to the cooled product. The reaction mixture in the flask was heated to reach 155° C. within 3 hours. The reaction mixture was continuously heated to the same temperature for one hour. Subsequently, the pressure of inside of the flask was reduced to 50 mmHg, and the heating was continued for 2 hours. Finally obtained reaction product (Additive Compound B) was a brown liquid having 4.2 wt. % of nitrogen content and 0.2 wt. % of boron content (boron/nitrogen=0.05).

Example 4

The below-mentioned additives and base oil were mixed to give a lubricating oil composition of the present invention.

|  | Weight % |
|---|---|
| Succinimide | 3.0 |
| Borated succinimide | 1.5 |
| Overbased calcium sulfonate | 0.08 |
| Reaction product A1 | 1.5 |
| Oleic acid | 0.25 |
| Dioctyldiphenylamine | 0.4 |
| 2,6-Di-t-butylphenol | 0.25 |
| Diphenyl hydrogen phosphite | 0.15 |
| Tolyltriazole | 0.1 |
| Silicone oil (anti-foaming agent) | 0.002 |
| Nitrogen-containing polymethacrylate | 5.7 |
| Base oil (purified mineral oil) | 87.068 |

Example 5

The procedures of Example 4 were repeated except for replacing Additive Compound A1 with Additive Compound A2, to give a lubricating oil composition of the present invention.

Example 6

The procedures of Example 4 were repeated except for replacing Additive Compound A1 with Borated Additive Compound B, to give a lubricating oil composition of the present invention.

Comparative Example A

The procedures of Example 4 were repeated except no Additive Compound A1 was used and changing the amount of the base oil to 88.568 wt %, to give a lubricating oil composition for comparison.

Comparative Example B

The procedures of Example 4 were repeated except for replacing Additive Compound A1 with the same amount of an amide compound (imidazoline-amide mixture produced by the reaction of 3 moles of isostearic acid and 1 mole of tetraethylenepentamine), to give a lubricating oil composition for comparison.

Comparative Example C

The procedures of Example 4 were repeated except for replacing Additive Compound A1 with the same amount of an imide compound (succinimide produced by the reaction of 2 moles of isooctadecenylsuccinic anhydride and 1 mole of diethylenetriamine), to give a lubricating oil composition for comparison.

Each of the lubricating oil compositions of Examples 4 to 6 and Comparative Examples A to C was examined for its shudder inhibition performance retention and transmissive torque capacity according to the following measuring procedures. The results are set forth in Table 2.

(1) Shudder Inhibition Performance Retention

The shudder inhibition was measured according to Shudder Inhibition Performance Test Method for Automobiles and Automobile Automatic Transmission Fluid (defined in JASO M349.2001). In the measurements, an LVFA (Low Velocity Friction Apparatus) tester was employed, and dμ/dV (0.3) and dμ/dV (0.9) were determined under the following test conditions:

Test Conditions
  Friction material: ZDR 522. OK, Steel plate (FZ132-8Y2)
  Oil volume: 150 mL
Break-in Operation
  Oil temperature: 80° C., Surface pressure: 1 MPa,
  Sliding rate: 0.6 m/s, Period: 30 min.

After the break-in operation was complete, the friction character was measured according to the below-stated μ-V character-measuring conditions.

μ-V Character-Measuring Conditions
  Oil temperature: 40° C., 80° C., 120° C.,
  Surface pressure: 1 MPa, Sliding rate: 0 to 1.5 m/s After the first measurement of μ-V character was complete, the retention ability was evaluated by measuring μ-V character at the lapse of the predetermined period of time by repeating the same measuring procedure.

Retention ability conditions
  Oil temperature: 120° C., Surface pressure: 1 MPa,
  Sliding rate: 0.9 m/s, Sliding period: 30 min.
  Rest: one min., Measurement: Every 24 hours
Measurements
  dμ/dV (0.3): dμ/dV (m/s) at sliding rate of 0.3 m/s
  dμ/dV (0.9): dμ/dV (m/s) at sliding rate of 0.9 m/s Shudder life: period of time until one of dμ/dV (0.3) and dμ/dV (0.9) became a minus value. A shorter period was adopted as the shudder life.

(2) Transmissive Torque Capacity

Dynamic friction test and static friction test were carried out by means of SAE No.2 Tester according to Friction Test Method for Automobiles and Automobile Automatic Transmission Fluid (defined in JASO M348.2002).

Friction Material
Friction material: FZ127-24-Y12, Steel plate (FZ132-8Y2)

Dynamic Friction Measurement
Inertial moment of inertia disc: 0.343 kg·m²
Oil temperature: 100° C.
Rotation: 3,600 rpm
Surface pressure of friction plate: 785 MPa
Test cycle: 30 sec./cycle, Test number: 5,000 cycles Static Friction Measurement
Rotation: 0.7 rpm
Oil temperature: 100° C.
Surface pressure of friction plate: 785 MPa
Test period: 3 min. after initiation of rotation
Test cycle: after 1, 5, 10, 20, 50, 100, 200, 500, 1000, 2000, 3000, 4000, and 5000 cycles Measurement
Static friction coefficient (μs) at the maximum torque caused when the rotation at 0.7 rpm starts and static coefficient (μt) at the lapse of 2 seconds.

Transmission torque capacity was evaluated by the value of μt. The μt value larger than 0.100 means that the transmission torque capacity is high, and a further larger μt value means a higher transmission torque capacity.

TABLE 2

Shudder Inhibition Performance

| | Shudder Inhibition Life (hr.) | μt after 20 cycles | μt after 500 cycles | μt after 1000 cycles |
|---|---|---|---|---|
| Example 4 | 552 | 0.136 | 0.135 | 0.131 |
| Example 5 | 504 | 0.132 | 0.133 | 0.130 |
| Example 6 | 528 | 0.135 | 0.138 | 0.133 |
| Comp. Ex. A | 24 | 0.142 | 0.140 | 0.139 |
| Comp. Ex. B | 216 | 0.094 | 0.089 | 0.086 |
| Comp. Ex. C | 168 | 0.126 | 0.119 | 0.123 |

The results set forth in Table 2 indicate that the lubricating oil compositions of the present invention (Examples 4 to 6) show a long shudder inhibition life (which means a long shudder inhibition capacity retention) and a high μt value such as a value exceeding 0.130 (which means a high transmissive torque capacity). In contrast, the comparative lubricating oil composition containing neither the amide compound nor the imide compound (Comparative Example A) shows a short shudder inhibition life while the μt value is high. The comparative lubricating oil compositions containing a conventional amide compound or imide compound (Comparative Examples B and C) show a low μt value and only a slightly longer shudder inhibition life (longer than the life of the lubricating oil composition of Comparative Example A) but shorter than the lubricating oil compositions of the present invention (Examples 4 to 6).

What is claimed is:

1. An additive compound comprising the reaction product of a linear or branched, saturated or unsaturated monovalent aliphatic acid having 8 to 22 carbon atoms, urea, and polyalkylenepolyamine, wherein said polyalkylenepolyamine contains 2 to 30 carbon atoms and 2 to 15 nitrogen atoms, wherein at least two of said nitrogen atoms are in the form of primary amines, and wherein the reaction product is non-borated, borated or a mixture thereof.

2. The additive compound of claim 1, wherein the reaction product is borated.

3. The additive compound of claim 1, wherein the reaction product is produced by reacting one mole of a linear or branched, saturated or unsaturated monovalent aliphatic acid having 8 to 22 carbon atoms, 0.01 to 2 moles of urea, and 0.1 to 1 mole of polyalkylenepolyamine.

4. The additive compound of claim 1, wherein the polyalkylenepolyamine is selected from the group consisting of ethylenediamine, diethylenetriamine, triethylenetetramine, tetraethylenepentamine, pentaethylenehexamine, and hexaethyleneheptamine.

5. The additive compound of claim 4, wherein the polyalkylenepolyamine is hexaethyleneheptamine.

6. The additive compound of claim 1, wherein the aliphatic acid is isostearic acid.

7. A lubricating oil composition comprising a major amount of base oil of lubricating viscosity and a minor amount of the reaction product of a linear or branched, saturated or unsaturated monovalent aliphatic acid having 8 to 22 carbon atoms, urea, and polyalkylenepolyamine, wherein said polyalkylenepolyamine contains 2 to 30 carbon atoms and 2 to 15 nitrogen atoms, wherein at least two of said nitrogen atoms are in the form of primary amines and wherein the reaction product is non-borated, borated or a mixture thereof.

8. The lubricating oil composition of claim 7, wherein the reaction product is borated.

9. The lubricating oil composition of claim 7, wherein the reaction product is produced by reacting one mole of a linear or branched, saturated or unsaturated monovalent aliphatic acid having 8 to 22 carbon atoms, 0.01 to 2 moles of urea, and 0.1 to 1 mole of polyalkylenepolyamine.

10. The lubricating oil composition of claim 7, wherein the polyalkylenepolyamine is selected from the group consisting of ethylenediamine, diethylenetriamine, triethylenetetramine, tetraethylenepentamine, pentaethylenehexamine, and hexaethyleneheptamine.

11. The lubricating oil composition of claim 10, wherein the polyalkylenepolyamine is hexaethyleneheptamine.

12. The lubricating oil composition of claim 7, wherein the aliphatic acid is isostearic acid.

13. The lubricating oil composition of claim 7, which further contains 0.01 to 2 wt. % of diphenyl hydrogen phosphite.

14. The lubricating oil composition of claim 7, which further contains a metal-containing detergent, an ashless dispersant, and an oxidation inhibitor.

15. An automatic transmission apparatus containing the lubricating oil composition of claim 7.

16. A method for reducing shudder in an automatic transmission of an internal combustion engine, said method comprising adding the lubricating oil composition of claim 7 to the automatic transmission and operating the engine.

* * * * *